United States Patent [19]

Miller

[11] Patent Number: 5,358,487

[45] Date of Patent: Oct. 25, 1994

[54] FRANGIBLE BALLOON CATHETER

[75] Inventor: Jay F. Miller, Miramar, Fla.

[73] Assignee: Cordis Corporation, Miami Lakes, Fla.

[21] Appl. No.: 137,631

[22] Filed: Oct. 15, 1993

[51] Int. Cl.$^5$ .................. A61M 29/00; A61M 31/00
[52] U.S. Cl. .......................... 604/96; 604/53
[58] Field of Search .................. 604/96–103; 606/191–196

[56] References Cited

U.S. PATENT DOCUMENTS

| 1,690,995 | 11/1928 | Pratt | 606/192 |
| 3,173,418 | 3/1965 | Baran | 604/101 |
| 3,211,152 | 10/1965 | Stern | 604/101 |
| 4,328,056 | 5/1982 | Snooks | 604/96 |
| 4,338,942 | 7/1982 | Fogarty | 606/194 |
| 4,744,366 | 5/1988 | Jang | 604/101 |
| 4,994,033 | 2/1991 | Shockey et al. | 604/194 |

Primary Examiner—John D. Yasko
Assistant Examiner—Frank Wilkens, III
Attorney, Agent, or Firm—Gerstman, Ellis & McMillin, Ltd.

[57] ABSTRACT

A balloon catheter comprises a catheter shaft, an inflation lumen defined in the catheter shaft, an inner balloon attached to the catheter shaft, with the interior of the inner balloon communicating with the inflation lumen, and an outer balloon surrounding the inner balloon. The inner balloon can be expanded by applying pressurized fluid through the inflation lumen for expansion of the inner and outer balloons, with the outer balloon being driven to expansion by the inner balloon. The inner balloon has a maximum inflation diameter which cannot be exceeded without bursting, while the outer balloon is capable of inflation to a diameter which is at least about 10 percent greater than the maximum inflation diameter of the inner balloon. Thus, upon further inflation, the inner balloon breaks at a predetermined diameter, permitting the outer balloon to be further expanded by further addition of inflation fluid through the lumen. Thus two balloons are controlled by a single inflation lumen.

14 Claims, 1 Drawing Sheet

FRANGIBLE BALLOON CATHETER

BACKGROUND OF THE INVENTION

Balloon catheters for angioplasty and other tissue expansion procedures are of course well known and in common clinical use. It is also known to provide angioplasty catheters which have a pair or more of balloons, one positioned inside the other, to permit the balloon assembly to be expanded to different, predetermined diameters by selective pressurization of the respective balloons through separate lumens. See for example Jang U.S. Pat. No. 4,744,366; Sahota U.S. Pat. No. 4,983,167; and Fogarty U.S. Pat. No. 4,338,942.

Multiple balloon catheters of the prior art require multiple inflation lumens, where the balloons are fluid impermeable, to permit the separate, independent inflation control of the respective balloons. However, the necessity for multiple inflation lumens requires that the diameter of the balloon catheter shaft must be larger than it otherwise would have to be, to accommodate such multiple inflation lumens.

In accordance with this invention, a balloon catheter for angioplasty or the like is provided in which multiple balloons are carried, one inside the other, on a catheter, being both controlled by a single inflation lumen even though the balloons are impermeable to the inflation medium. Nevertheless, the balloons may be inflated to differing diameters to provide an improvement in the versatility of use, which is so desired in angioplasty catheters and the like. This is coupled with a small diameter for the catheter shaft, since only one inflation lumen is required for two or more balloons.

Additionally, the balloon catheter of this invention can exhibit an expansion of a first, inner balloon at a first pressure/expansion gradient which exhibits a lesser amount of expansion per unit increase of pressure. Then, when the second balloon is expanded by itself, apart from the first balloon, to a greater diameter beyond the maximum expansion of the first balloon, it can typically expand at a second pressure/expansion gradient which has a greater amount of expansion per unit increase of pressure than the first pressure/expansion gradient. This is believed to provide a clinical advantage in the field of angioplasty, in that the first pressure/expansion gradient may be of a particularly desirable range to crack a hard stenosis in an artery as the inner balloon expands. Then, the second pressure/expansion gradient is more favorable for the expansion of the stenosis after it has been broken, and the initial resistance has been overcome by the expanding balloon. Also by this invention, the same catheter may provide differing balloon maximum inflation diameters for greater versatility.

DESCRIPTION OF THE INVENTION

In accordance with this invention, a method is providing of inserting a catheter into the arterial system of a patient, and pressurizing a lumen of the catheter to cause a catheter balloon portion thereof to expand. The catheter balloon portion comprises an inner balloon surrounded by a separate, outer balloon, both of which are essentially impermeable to the inflation fluid used. The outer balloon has a greater maximum diameter than the inner balloon. The method comprises the step of increasingly pressurizing the lumen at a first pressure/expansion gradient which is defined primarily by the inner balloon to expand the balloons together until the inner balloon breaks. Thereafter, one further pressurizes the lumen to further expand the outer balloon at a second pressure/expansion gradient.

A third or a fourth surrounding balloon may also be used, each of a larger maximum diameter, all being expandable to a greater diameter from a single inflation lumen when the balloons inside them break.

Typically, the outer balloon comprises a flexible but inelastic material such as nylon 12 or poly(ethylene terephthalate) (PET), which are materials conventionally used in angioplasty catheter balloons. The inner catheter balloon (or balloons) may, if desired, be made of an elastomeric material such as a latex, although it may also be made of a flexible, inelastic material, particularly when it is desired to precisely control the maximum amount of expansion of the inner balloon or balloons.

It is also desirable, as previously stated, for the material and characteristics of the first and second balloons to be selected so that the pressure/expansion gradient of the second balloon, as it independently expands free of the first balloon, exhibits a greater amount of expansion per unit increase of pressure than the first pressure/expansion gradient of the first balloon as it expands, pushing the second balloon outwardly with it.

The outer balloon preferably has greater tensile strength than the inner balloon, since the inner balloon is intended to break in the process of this invention.

The catheter of this invention comprises a catheter shaft; an inflation lumen defined in the catheter shaft; and an inner balloon attached to the catheter shaft, the interior of the inner balloon communicating with the inflation lumen. Also, an outer balloon surrounds the inner balloon and is sealed to the catheter.

The inner balloon can be expanded by applying pressurized fluid through the inflation lumen to the inner balloon interior, to cause expansion of both the inner and outer balloons. The inner balloon has a maximum inflation diameter which cannot be exceeded without bursting. The outer balloon is capable of inflation to a diameter which is at least 10 percent greater than the maximum inflation diameter of the inner balloon.

Typically, the catheter of this invention has only a single inflation lumen which communicates with the inner balloon, while the outer balloon has no other inflation lumen communicating with it, so that the outer balloon is expanded exclusively by expansion of the inner balloon, and then by pressurized fluid from the inflation lumen after breakage of the inner balloon.

DESCRIPTION OF SPECIFIC EMBODIMENT

Figure 1:
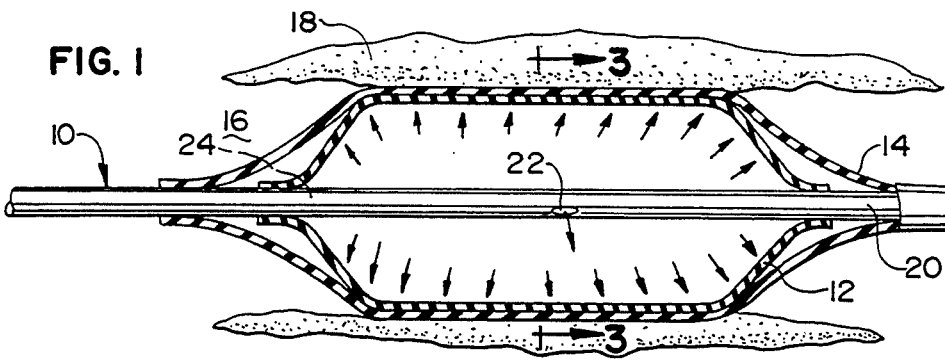
FIG. 1 is an enlarged, elevational view, taken partly in longitudinal section, of the distal portion of an angioplasty catheter made in accordance with this invention, with the inner balloon being shown under maximum inflation.

Referring to the drawings, FIG. 1 shows the distal end of an angioplasty catheter 10 having a catheter balloon assembly which comprises an inner balloon 12 and an outer balloon 14, positioned within an artery 16 which has a partial stenotic blockage 18. Except as otherwise shown, catheter 10 may be of entirely conventional design. Central catheter shaft 20 may be a hollow plastic member, or it may be of the "balloon on a wire" type design, both of these being intended to be included in the term "catheter". At least central, major portions of balloons 12, 14 are free of attachment to each other.

Catheter shaft 20 defines a single inflation lumen 24, and a side port 22, which causes inflation lumen 24 to communicate with the interior of inner balloon 12. Catheter shaft 20 may or may not have an additional lumen which passes through the entire length thereof, for fluid communication throughout the length of the catheter between the proximal end and the distal end 26 thereof.

Figure 3:
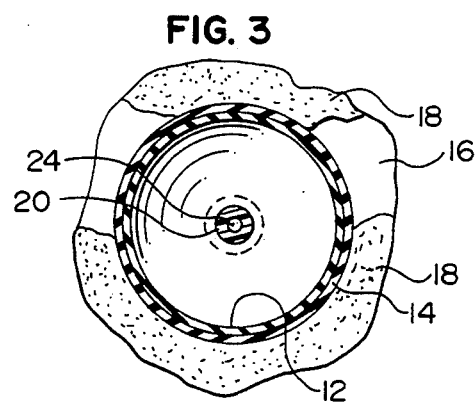
FIG. 3 is a sectional view taken along line 3—3 of FIG. 1.
Figure 4:
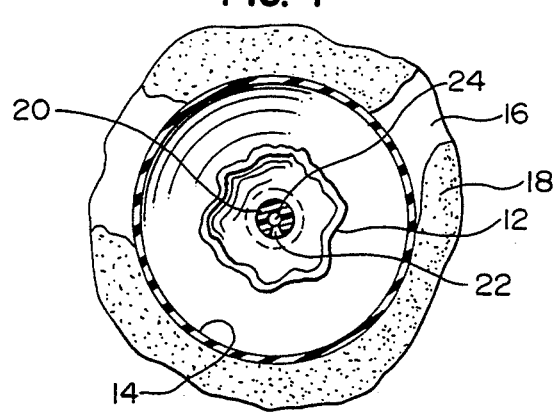
FIG. 4 is a sectional view taken along line 4—4 of FIG. 2.

In accordance with this invention, FIGS. 1 and 3 show the distal catheter portion positioned for balloon expansion of a stenosis 18, with the inner balloon 12 being already expanded to essentially its maximum amount. Balloon 12 may be made of an elastomeric material which exhibits, therefore, a resistance to expansion as it stretches outwardly. Thus, because of this resistance, the degree of radially outward expansion of balloon 12 as the internal pressure is increased by the flow of inflation fluid through port 22 is relatively low. Thus, balloon 12 expands at a first pressure/expansion gradient.

Figure 2:
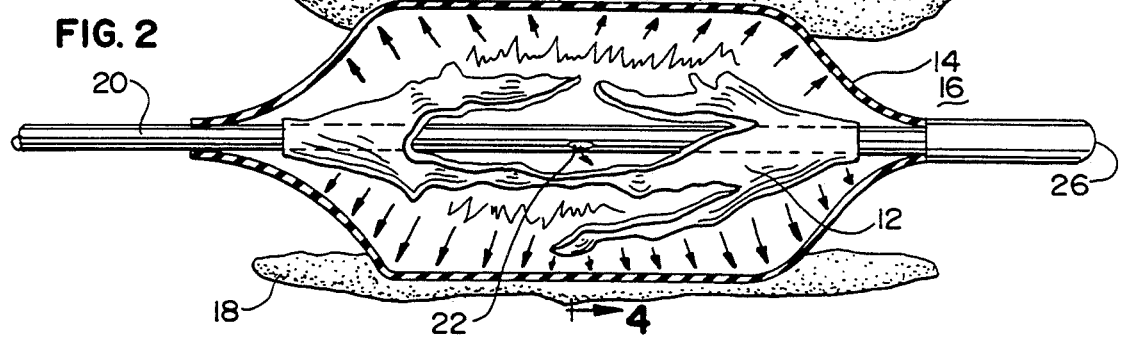
FIG. 2 is an elevational view similar to FIG. 1, showing the inner balloon having burst and the outer balloon being further inflated to its maximum inflation.

As shown in FIG. 2, at a predetermined expansion pressure and diameter of balloon 12, it bursts. At that point, the elastic resistance of balloon 12 ceases, typically causing a slight retraction of outer balloon 14, which up to this moment has been expanded purely by the expansion action of inner balloon 12.

Then, with the bursting of balloon 12, the inflation fluid from inflation lumen 24 and port 22 enters into direct contact with balloon 14. The further introduction of pressurized inflation fluid can cause the further expansion of balloon 14, as shown in FIG. 2. Also, the bursting of the balloon can typically be detected at the proximal end of the catheter by a sudden, small pressure fluctuation, to serve as an indication of balloon breakage.

Thereafter, as the second balloon 14 is expanded without the influence of inner balloon 12, its pressure/expansion gradient is typically different from the first pressure/expansion gradient, which was present when the situation was governed by the expansion of balloon 12. Typically, the second pressure/expansion gradient of balloon 14 in the phase shown in FIG. 2 is greater than the first pressure/expansion gradient, with more radial expansion taking place per unit increase of pressure as provided by the inflation fluid passing through port 22.

Thus, the physician has a different type of action in the balloon expansion in accordance with this invention. Initially, the expansion is lower as the pressure is increased. Then, after breakage of inner balloon 12, the pressure expansion increases, all else being equal, per unit increase of pressure, relative to the first pressure/expansion gradient.

If desired, inner balloon 12 may be made of a flexible but inelastic material such as nylon or PET rather than an elastomer, similar to the composition of outer balloon 14, so that inner balloon 12 expands before break to a more controllable maximum diameter. Nevertheless, when it breaks, it then becomes possible to expand outer balloon 14 to its maximum diameter. Thus it may be possible to avoid the need to replace the catheter with one with a larger balloon, since the physician has more than one balloon expansion diameter to work with.

The wall thicknesses of the respective balloons may be generally conventional and appropriate for the desired performance parameters.

The above has been offered for illustrative purposes only, and is not intended to limit the scope of the invention of this application, which is as defined in the claims below.

That which is claimed is:

1. The method of inserting a catheter into the arterial system of a patient and pressurizing an inflation lumen of said catheter to cause a catheter balloon portion to expand, said catheter balloon portion comprising an inner balloon surrounded by a separate outer balloon, said outer balloon having greater maximum inflated diameter than said inner balloon, said method comprising the step of pressurizing said lumen at a first pressure/expansion gradient to expand said balloons until said inner balloon breaks, and thereafter further pressurizing said lumen to further expand said outer balloon at a second pressure/expansion gradient.

2. The method of claim 1 in which said second pressure/expansion gradient exhibits a greater amount of expansion per unit increase of pressure than the first pressure/expansion gradient.

3. The method of claim 1 in which said inner balloon is made of a material which is more elastic than the material of said outer balloon.

4. The method of claim 1 in which said outer balloon has greater tensile strength than said inner balloon.

5. The method of claim 1 in which said inner balloon is made of a material which is more elastic than the material of said outer balloon, and in which said outer balloon has greater tensile strength than said inner balloon.

6. The method of claim 5 in which said second pressure/expansion gradient exhibits a greater amount of expansion per unit increase of pressure than the first pressure/expansion gradient.

7. The method of claim 6 in which said outer balloon is made out of a flexible but essentially non-elastic nylon or poly(ethylene terephthalate).

8. The method of claim 1 in which said second pressure/expansion gradient exhibits a greater amount of expansion per unit increase of pressure than the first pressure/expansion gradient.

9. The method of claim 1 in which said outer balloon is made out of a flexible but essentially non-elastic nylon or poly(ethylene terephthalate).

10. A balloon catheter which comprises a catheter shaft; and inflation lumen defined in said catheter shaft; and inner balloon attached to said catheter shaft, the interior of said inner balloon communicating with said inflation lumen; and an outer balloon surrounding said inner balloon, said outer balloon being free of direct communication with an inflation lumen, whereby said inner balloon can be expanded by applying pressurized fluid through said inflation lumen to the inner balloon interior to cause expansion of said inner and outer balloons, said inner balloon having a maximum inflation diameter which cannot be exceeded without bursting, said inner balloon being formed to expand at a first pressure/expansion gradient, said outer balloon being capable of expansion to a diameter beyond the maximum expansion diameter of said inner balloon, whereby further expansion of said inner and outer balloons causes the inner balloon to break, and the outer balloon to expand at a second pressure/expansion gradient which exhibits a greater amount of expansion per unit increase of pressure to a maximum expansion than the first pressure/expansion gradient; said outer balloon being capable of inflation to a diameter which is at least 10 percent greater than said maximum inflation diameter of the inner balloon, said inner balloon being made of a material that is more elastic than the material of the outer balloon.

11. The balloon catheter of claim 10 in which at least central, major portions of said inner and outer balloons are free of attachment to each other.

12. The balloon catheter of claim 11 in which said outer balloon has greater tensile strength than said inner balloon.

13. The balloon catheter of claim 12 in which said outer balloon is made of a flexible but essentially non-elastic nylon or poly(ethylene terephthalate).

14. The balloon catheter of claim 13 in which said inner balloon is in direct physical contact with said outer balloon during at least the majority of expansion of said inner balloon, to force expansion of said outer balloon.

* * * * *